(12) United States Patent
Harris et al.

(10) Patent No.: US 7,659,086 B2
(45) Date of Patent: Feb. 9, 2010

(54) IMMUNOASSAY EMPLOYING TWO-STEP INTERNAL CALIBRATION REACTION

(75) Inventors: Paul C. Harris, Bothell, WA (US); Whalley K. Fong, Coquitlam (CA); Lynn Cloney, Vancouver (CA)

(73) Assignee: Response Biomedical Corporation, Vancouver, British Columbia (CA)

( * ) Notice: Subject to any disclaimer, the term of this patent is extended or adjusted under 35 U.S.C. 154(b) by 370 days.

(21) Appl. No.: 11/805,281

(22) Filed: May 22, 2007

(65) Prior Publication Data

US 2007/0287197 A1    Dec. 13, 2007

Related U.S. Application Data

(63) Continuation of application No. PCT/US2005/042668, filed on Nov. 22, 2005.

(60) Provisional application No. 60/630,866, filed on Nov. 23, 2004.

(51) Int. Cl.
*G01N 33/53* (2006.01)

(52) U.S. Cl. .................. 435/7.9; 435/7.1; 435/7.94; 435/7.2; 435/287.1; 435/287.9; 435/805; 435/810; 436/514; 436/518; 422/100

(58) Field of Classification Search .................. 435/7.1, 435/7.94, 7.2, 287.1, 287.9, 805, 810; 436/518, 436/514; 422/100

See application file for complete search history.

(56) References Cited

U.S. PATENT DOCUMENTS

| | | | | |
|---|---|---|---|---|
| 5,424,220 | A | * | 6/1995 | Goerlach-Graw et al. ... 436/518 |
| 6,436,721 | B1 | * | 8/2002 | Kuo et al. ................. 436/514 |
| 6,482,362 | B1 | * | 11/2002 | Smith ...................... 422/100 |
| 7,175,992 | B2 | | 2/2007 | Fong |
| 2003/0124739 | A1 | | 7/2003 | Song et al. |
| 2003/0199004 | A1 | | 10/2003 | Fong |
| 2005/0074902 | A1 | * | 4/2005 | Laroche .................... 436/518 |
| 2006/0223193 | A1 | * | 10/2006 | Song et al. ................ 436/514 |

FOREIGN PATENT DOCUMENTS

| | | |
|---|---|---|
| JP | 2001033454 | 2/2001 |
| WO | WO 97/09620 | 3/1997 |
| WO | WO 2006/083367 A2 | 8/2006 |

* cited by examiner

*Primary Examiner*—Bao-Thuy L Nguyen
(74) *Attorney, Agent, or Firm*—Hamilton, Brook, Smith & Reynolds, P.C.

(57) ABSTRACT

Methods for quantitatively measuring the amount of an analyte of interest in a fluid sample, and kits useful in the methods, are disclosed. The methods comprise sandwich assays, and utilize an internal calibration reaction that closely mimics the reaction of test particles by the use of a two-step reaction.

12 Claims, 3 Drawing Sheets

IMMUNOASSAY EMPLOYING TWO-STEP INTERNAL CALIBRATION REACTION

RELATED APPLICATIONS

This application is a continuation of International Application No. PCT/US2005/042668, which designated the United States and was filed on Nov. 22, 2005, published in English, which claims the benefit of U.S. Provisional Application No. 60/630,866, filed on Nov. 23, 2004. The entire teachings of the above applications are incorporated herein by reference.

BACKGROUND OF THE INVENTION

Quantitative analysis of cells and analytes in fluid samples, particularly bodily fluid samples, often provides critical diagnostic and treatment information for physicians and patients. Quantitative immunoassays utilize the specificity of the antigen (Ag)-antibody (Ab) reaction to detect and quantitate the amount of an Ag or Ab in a sample. In solid phase immunoassays, one reagent (e.g., the Ag or Ab) is attached to a solid surface, facilitating separation of bound reagents or analytes from free reagents or analytes. The solid phase is exposed to a sample containing the analyte, which binds to its Ag or Ab; the extent of this binding is quantitated to provide a measure of the analyte concentration in the sample. Transduction of the binding event into a measurable signal, however, is affected by a number of limitations, including constraints of particle movement on the solid phase, which affect the specificity and applicability of quantitative immunoassays

SUMMARY OF THE INVENTION

The present invention pertains to methods for quantitatively measuring the amount of an analyte of interest in a sample. The methods employ an analyte binding agent, which can be a member of a specific binding pair together with the analyte of interest. In certain embodiments, the analyte binding agent can be, for example, an antibody; an antibody fragment; a hapten; a drug conjugate; or a receptor. The methods also employ a calibration analyte and the calibration analyte binding agent; these can also be members of a specific binding pair. In certain embodiments, the calibration analyte binding agent can be, for example, an antibody; an antibody fragment; a hapten; a drug conjugate; or a receptor. If the analyte binding agent is an antibody, the sample capture reagent can also be an antibody, such as an antibody directed against the same epitope of the analyte as the antibody on the binding particles, or an antibody directed against a different epitope of the analyte as the antibody on the binding particles. If the calibration analyte binding agent is an antibody, the calibration capture reagent can be, for example, an antibody directed against the same epitope of the calibration analyte as the antibody on the binding particles, or an antibody directed against a different epitope of the calibration analyte as the antibody on the binding particles.

The methods also utilize a solid phase apparatus comprising a membrane strip comprising an application point, a sample capture zone and a calibration capture zone, wherein the sample capture zone is between the contact region and the calibration capture zone; and a sample collection apparatus that is not in fluid contact with the solid phase apparatus. The sample collection apparatus contains either: i) a population of binding particles, wherein the binding particles are coated with both an analyte binding agent and a calibration analyte binding agent; or ii) a population of analyte binding particles, wherein the analyte binding particles are coated with an analyte binding agent, and a population of calibration binding particles, wherein the calibration binding particles are coated with a calibration binding agent. The sample collection apparatus may also contain a calibration analyte; if so, the population of particles is located at a different place in the sample collection apparatus from the calibration analyte. In certain embodiments, the binding particles, or analyte binding particles and calibration binding particles, are evaporatively-dried, vacuum-dried or freeze-dried in the sample collection apparatus. The calibration analyte can also be evaporatively-dried, vacuum-dried or freeze-dried in the sample collection apparatus.

To perform the assays, the sample to be assayed for the analyte of interest is introduced into the sample collection apparatus, and a buffer is subsequently introduced into the sample collection apparatus; alternatively, a buffer is introduced into the sample collection apparatus, and subsequently the sample is introduced into the sample collection apparatus. If there is no calibration analyte in the sample collection apparatus, then the buffer contains calibration analyte. The buffered, mixed fluid sample contains contacted binding particles (e.g., binding particles having calibration analyte bound thereon and/or having analyte of interest bound thereon; and/or binding particles having neither calibration analyte nor analyte of interest bound thereon; or analyte binding particles having analyte of interest bound thereon; analyte binding particles not having analyte of interest bound thereon; calibration binding particles having calibration analyte bound thereon; and calibration binding particles not having calibration analyte bound thereon).

The buffered, mixed fluid sample is applied to the application point of the membrane strip, and the strip is maintained under conditions which allow fluid to transport contacted binding particles by capillary action through the strip to and through the sample capture zone that has a sample capture reagent immobilized thereon. The sample capture reagent can bind to analyte of interest, and thereby can interact with binding particles having analyte of interest bound thereon. The strip is further maintained under conditions which allow the fluid in the sample to transport contacted binding particles by capillary action through the strip to and through the calibration capture zone that has a calibration capture reagent immobilized thereon. The calibration capture reagent can bind to the calibration analyte, and thereby can interact with binding particles having calibration analyte bound thereon. The membrane strip is further maintained under conditions which allow the fluid in the sample to transport contacted binding particles not bound to the sample capture reagent or to the calibration capture reagent by capillary action beyond the calibration capture zone, such as into a wicking pad.

To determine the amount of analyte of interest in the sample, the amount of binding particles in the sample capture zone and the amount of binding particles in the calibration capture zone are assessed, and a corrected binding particle amount is determined from the amount of binding particles in the sample capture zone and the amount of binding particles in the calibration capture zone. The amount of analyte of interest in the sample is directly related to the corrected binding particle amount. In certain embodiments, the corrected binding particle amount is determined as a ratio of the amount of binding particles in the sample capture zone, to the amount of binding particles in the calibration capture zone; in other embodiments, the corrected binding particle amount is determined as a ratio of the amount of binding particles in the sample capture zone, to the sum of the amount of binding particles in the calibration capture zone and the amount of binding particles in the sample capture zone.

The assays of the present invention provide an internal calibration reaction that closely mimics the reaction of the test particles by the use of a two-step reaction, and thereby allows more accurate determination of the amount of an analyte of interest in a sample.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figures 1, 2, 3:
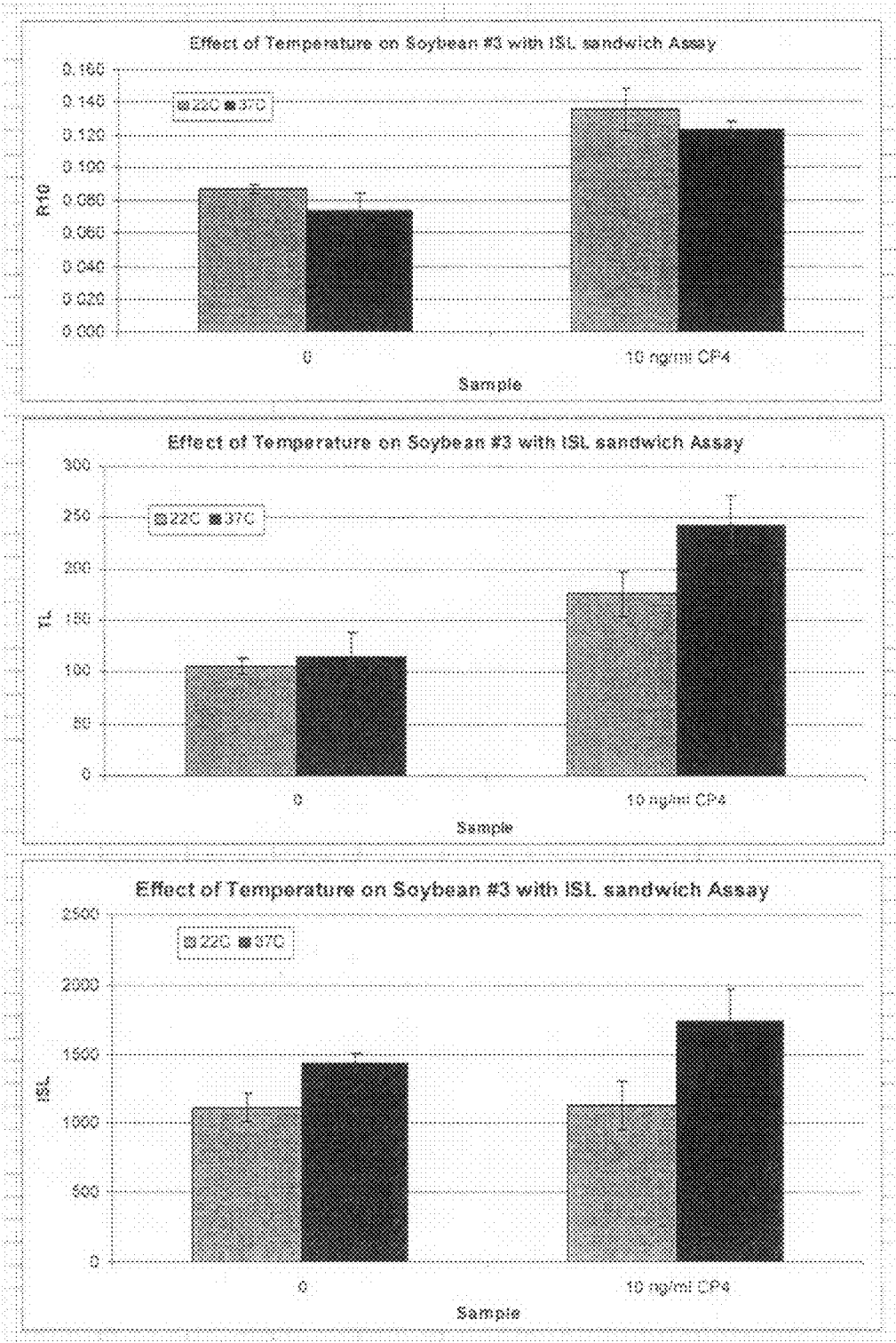
FIG. 1 is a graphic depiction of ratios of particles detected at the sample capture zone, to those detected at the calibration capture zone, indicating the presence of compensation for temperature effects. TL=Test Line (sample capture zone); ISL=Internal Standard Line (calibration capture zone); R10=Ratio (TL/TL+ISL).
FIG. 2 is a graphic depiction of the effect of temperature on capture of particles at the sample capture zone.
FIG. 3 is a graphic depiction of the effect of temperature on capture of particles at the calibration capture zone.

A description of preferred embodiments of the invention follows.

The present invention pertains to methods of quantitatively measuring the amount of an analyte in a sample using assays, particularly quantitative immunochromatographic assays, and kits therefor.

An "assay," as used herein, refers to an in vitro procedure for analysis of a sample to determine the presence, absence, or quantity of one or more analytes of interest. The assays of the inventions utilize an analyte binding agent; the analyte of interest and the analyte binding agent are members of a specific "binding pair," in which a first member of the binding pair (e.g., analyte) reacts specifically with a second member (e.g., the binding agent). Specific interaction between the members of the binding pair indicates that the first member of the binding pair preferentially binds or otherwise interacts with the second member of the binding pair, preferably to the exclusion of any binding to another compound in the assay. Together, the analyte of interest and the analyte binding agent are referred to herein as the "analyte specific binding pair". One or both members of the analyte specific binding pair can be an antibody. For example, a first member of the binding pair (e.g., an analyte of interest) can be an antibody, and a second member of the binding pair (e.g., a binding agent) can be anti-immunoglobulin antibody. Alternatively, the first member of the binding pair (e.g., the analyte) can be an antigen, and the second member of the binding pair (e.g., the binding agent) can be an antibody; or the first member of the binding pair (e.g., the analyte) can be antibody, and the second member of the binding pair (e.g., the binding agent) can be an antigen.

The assays of the inventions additionally utilize a calibration analyte and a calibration analyte binding agent. The calibration analyte and the calibration analyte binding agent are similarly members of a specific binding pair in which the first member of the binding pair (e.g., calibration analyte) reacts specifically with the second member (e.g., the calibration analyte binding agent). As with regard to the analyte and the analyte binding agent, one or both members of the binding pair of the calibration analyte and the calibration analyte binding agent (together, the "calibration specific binding pair") can be an antibody. For example, a first member of the binding pair (e.g., the calibration analyte) can be an antibody, and a second member of the binding pair (e.g., the calibration analyte binding agent) can be anti-immunoglobulin antibody; alternatively, the first member of the binding pair (e.g., the calibration analyte) can be an antigen, and the second member of the binding pair (e.g., the calibration analyte binding agent) can be an antibody.

Alternatively, in other embodiments of the assays of the invention, none of the members of the analyte specific binding pair nor the calibration specific binding pair need be antibodies. For example, in one embodiment, the first member of a binding pair can be a ligand, and the second member of that binding pair can be a receptor; alternatively, the first member of an binding pair can be a lectin, and the second member of that binding pair can be a sugar. In still another embodiment, the first member of a binding pair can be a nucleic acid (e.g., DNA, RNA), and the second member of that binding pair can be a nucleic acid which specifically hybridizes to the first member of that binding pair.

"Specific hybridization," as used herein, refers to the ability of a first nucleic acid to hybridize to a second nucleic acid in a manner such that the first nucleic acid does not hybridize to any nucleic acid other than to the second nucleic acid (e.g., when the first nucleic acid has a higher similarity to the second nucleic acid than to any other nucleic acid in a sample wherein the hybridization is to be performed). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 70%, 75%, 80%, 85%, 90%, 95%). For example, certain high stringency conditions can be used which distinguish perfectly complementary nucleic acids from those of less complementarity.

"High stringency conditions", "moderate stringency conditions" and "low stringency conditions" for nucleic acid hybridizations are explained on pages 2.10.1-2.10.16 and pages 6.3.1-6.3.6 in *Current Protocols in Molecular Biology* (Ausubel, F. M. et al., "*Current Protocols in Molecular Biology*", John Wiley & Sons, (1998), the entire teachings of which are incorporated by reference herein). The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules.

In the methods of the invention, an assay is used. In one embodiment, the assay is an "immunoassay" which utilizes antibodies as a component of the procedure. In a preferred embodiment, the assay is a "sandwich" assay, which is a test for an analyte in which a fluid containing sample to be assessed for the presence or absence, or quantity of analyte, is contacted with particles coated with an analyte binding agent, such as antibodies to the analyte, and the resultant mixture is applied to a membrane and subsequently moves by capillary action through the membrane. A positive result is indicated by detection of interaction between analyte and analyte binding agent-coated particles in a capture zone of the membrane, the amount of analyte binding agent-coated particles in the capture zone being related to the amount of analyte in the fluid sample.

In the methods of the invention, a sample is assessed for the presence or absence, or quantity, of an analyte of interest. The term "analyte of interest," as used herein, refers to a first member of an analyte specific binding pair as described above. The analyte is a molecule or compound for which the amount will be measured. The analyte can be in the form of a solid, such as a dry substance (e.g., a powder, a particulate; spore; or other particle), or can be in the form of a fluid (e.g., a solid as described above that has been dissolved or suspended in a fluid; or other liquid sample). Examples of analytes include spores; proteins, such as hormones or enzymes; glycoproteins; peptides; small molecules; polysaccharides; lectins; antibodies; antibody fragments; nucleic acids; drugs; drug conjugates; toxins (e.g., environmental toxins); viruses or virus particles; bacteria; other infectious agents or products of infectious agents; portions of a cell wall; haptens; receptors; and other compounds. In a preferred embodiment, the analyte is "immunogenic," which indicates that antibodies (as described below) can be raised to the analyte, or to an analyte that is bound to a carrier (e.g., a hapten-carrier conjugate, for which antibodies can be raised to the hapten). In some representative embodiments, the analyte of interest can be myoglobin; CK-MB; troponin I; PSA; digoxin; theophylline; ricin; C-reactive protein; or b-natriuretic peptide. In other representative embodiments, the analyte of interest can be a hormone (e.g., T-3 or T-4) or a drug of abuse (LSD, THC, barbiturates, etc.). In still other representative embodiments, the analyte of interest can be an infectious agent or a product of an infectious agent, such as *Francisella tularensis* (the causative agent of tularemia); *Claustridia* or toxin produced thereby (botulinum toxin); Variola (smallpox) virus or other pox viruses (e.g., cowpox, monkey pox); or a spore of a type of *Bacillus*, such as *Bacillus anthracis* (anthrax) or *Bacillus globigii*. The analyte of interest can be in a liquid sample; alternatively, the analyte of interest can be in a dry (non-fluid) sample (e.g., a solid, such as a particulate sample, powder sample, or soil sample).

If the sample that is assessed for the presence or absence, or quantity, of the analyte of interest, is a fluid, it is a fluid that wets the membrane material; that supports a reaction between the analyte of interest and the analyte binding agent, such as the antibody/antigen reaction (i.e., does not interfere with antibody/antigen interaction); and that has a viscosity that is sufficiently low to allow movement of the fluid by capillary action. In a preferred embodiment, the fluid is an aqueous solution (such as a bodily fluid). A fluid sample can be a fluid having relatively few components, for example, an aqueous solution containing the analyte of interest; alternatively, a fluid sample can be a fluid having many components, such as a complex environmental sample (e.g., sewage, waste water, groundwater, or other water sample), or a complex biological fluid (e.g., whole blood, plasma, serum, urine, cerebrospinal fluid, saliva, semen, vitreous fluid, synovial fluid, or other biological fluid). In a preferred embodiment in which the fluid is a biological fluid, the fluid is whole blood, plasma, or serum. If desired, the fluid sample can be diluted; for example, if a complex biological fluid is used as the fluid sample, it can be diluted with a solution (e.g., an aqueous solution).

If the analyte of interest is not in solution (e.g., the analyte of interest is in a dry or solid sample, as described above), it can be extracted, suspended, or dissolved into a fluid. For example, if the analyte of interest is a nucleic acid, it can be extracted from cells of interest into a solution (e.g., an aqueous solution, such as the buffer described below); in another example, if the analyte of interest is a powder or particulate material (e.g., a powder, a particulate, a soil sample, or spores), it can be suspended or dissolved into a solution (e.g., an aqueous solution, such as the buffer described below) such as by obtaining a sample of the dry material (e.g., using a swab or other instrument) and placing the sample of dry material into the solution. Thus, a "fluid sample" can refer not only to a liquid sample to be assessed for an analyte of interest, but also to a fluid in which a solid material sample (to be assessed for an analyte of interest) is extracted, suspended or dissolved.

The "analyte binding agent," as used herein, refers to second member of a binding pair as described above. The analyte binding agent is a compound that specifically binds to the analyte (the first member of the binding pair), such as an antibody, a hapten or drug conjugate, a receptor, or another binding partner. In a preferred embodiment, the analyte binding agent is an antibody to the analyte of interest.

In a preferred embodiment of the invention, the analyte of interest and the calibration analyte have similar properties: for example, if the analyte of interest is a protein, the calibration analyte is a different protein. In another preferred embodiment of the invention, the analyte binding agent and the calibration analyte binding agent also have similar properties: for example, if the analyte binding agent is an antibody, the calibration analyte binding agent is also an antibody. In addition, the calibration analyte is an agent that is unlikely to appear in the sample being tested for the analyte of interest (for example, if the sample containing the analyte of interest is a blood sample, the calibration analyte preferably is an agent, such as a protein, that is not typically found in a blood sample), and is an agent that will not be cross-reactive with the analyte binding agent.

The "sandwich" assay of the invention utilizes a solid phase apparatus. The solid phase apparatus includes a membrane strip having an application point, a sample capture zone, and a calibration capture zone. The solid phase apparatus may optionally include a wicking pad following the calibration capture zone, and a sample pad adjacent to or covering the application point. The membrane strip can be made of a substance having the following characteristics: sufficient porosity to allow capillary action of fluid along its surface and through its interior; the ability to allow movement of coated particles (e.g., analyte binding particles, as described below) or complexes of particles and analyte of interest (e.g., contacted analyte binding particles, as described below) by capillary action (i.e., it must not block the particles or complexes of particles and analyte of interest); and the ability to be wet by the fluid containing the analyte. Examples of membrane substances include: cellulose, cellulose nitrate, cellulose acetate, glass fiber, nylon, polyelectrolyte ion exchange membrane, acrylic copolymer/nylon, and polyethersulfone. In a preferred embodiment, the membrane strip is made of cellulose nitrate (e.g., a cellulose nitrate membrane with a Mylar backing) or of glass fiber.

The "application point" is the position on the membrane where a fluid can be applied. An "application pad" can also optionally be used. For example, if the sample containing the analyte of interest contains particles or components that should preferentially be excluded from the immunoassay, an application pad can be used. The application pad typically can filter out particles or components that are larger (e.g., greater than approximately 2 to 5 microns) than the particles used in the methods of the invention (e.g., approximately 0.3-X microns) In one embodiment, for example, the sample containing the analyte of interest is a blood sample; to remove red blood cells, white blood cells, and other components, an application pad is used. Alternatively, for example, if the sample is an environmental or "dirty" sample, an application pad is used to substantially remove larger particles. If an application pad is used, it rests on the membrane, immediately adjacent to or covering the application point. The application pad can be made of an absorbent substance which can deliver a fluid sample, when applied to the pad, to the application point on the membrane. Representative substances include cellulose, cellulose nitrate, cellulose acetate, nylon, polyelectrolyte ion exchange membrane, acrylic copolymer/nylon, polyethersulfone, or glass fibers. In one embodiment, the pad is a Hemasep®-V pad (Pall Corporation). In another embodiment, the pad is a Pall 133, Pall A/D, or glass fiber pad.

If a wicking pad is present, as described above, it can similarly be made from such absorbent substances. In a preferred embodiment, a wicking pad is used, as it allows continuation of the flow of liquid by capillary action past the capture zones and facilitates the movement of nonbound particles away from the capture zones.

The "sample capture zone" refers to a point on the membrane strip at which a "sample capture reagent" is immobilized (e.g., coated on and/or permeated through the membrane). The sample capture reagent is an analyte binding agent, such as those described above. The sample capture reagent need not be the same analyte binding agent as described above; however, the sample capture reagent also forms a binding pair with the analyte of interest, in that it specifically and preferentially binds to the analyte of interest. In a preferred embodiment, the sample capture reagent is an antibody directed against the analyte; it can be directed against the same epitope of the analyte as, or against a different epitope of the analyte from, the epitope that binds to the antibodies used as analyte binding agents coated on the particles. For example, in certain embodiments in which the analyte expresses a multitude of an epitope (e.g., anthrax, a large bacterium that expresses many of the same antigenic epitopes on its surface), the sample capture reagent can be an antibody directed against the same epitope of the analyte as the epitope that is targeted by the analyte binding agents on the particles. In another example, in certain embodiments in which the analyte does not express a multitude of an epitope (e.g., troponin I, a small molecule that expresses a few different antigenic epitopes on its surface), the sample capture reagent can be an antibody directed against a different epitope of the analyte from the epitope that is targeted by the analyte binding agents on the particles.

In one preferred embodiment in which the analyte of interest is an antibody to an antigen, the analyte binding agent is antigen, and the sample capture reagent is an antibody to the antibody that is the analyte of interest. In this embodiment, there should be an excess of the sample capture reagent, because it will capture not only antibody that is bound to the antigen on the binding particles, but also to "free" antibody that is not bound to any particles.

The apparatus additionally includes a "calibration capture reagent" immobilized (e.g., coated on and/or permeated through the membrane) in a "calibration capture zone." The calibration capture reagent interacts with the calibration analyte, and does not interact with the analyte of interest. The calibration capture reagent is a calibration analyte binding agent, such as those described above. The calibration capture reagent need not be the same calibration analyte binding agent as described above; however, the calibration capture reagent also forms a binding pair with the calibration analyte, in that it specifically and preferentially binds to the calibration analyte. In a preferred embodiment, the calibration capture reagent is an antibody directed against the calibration analyte; it can be directed against the same epitope of the calibration analyte as, or against a different epitope of the calibration analyte from, the epitope that binds to the antibodies used as calibration analyte binding agents coated on the particles. In certain embodiments in which the calibration analyte expresses a multitude of an epitope, the calibration capture reagent can be an antibody directed against the same epitope of the calibration analyte as the epitope that is targeted by the calibration analyte binding agent on the calibration analyte binding particles (as described below). In another example, in certain embodiments in which the calibration analyte does not express a multitude of an epitope, the calibration capture reagent can be an antibody directed against a different epitope of the calibration analyte from the epitope that is targeted by the calibration analyte binding agents on the calibration analyte binding particles.

The calibration capture zone is positioned such that the sample capture zone is between the application point and the calibration capture zone. In a preferred embodiment, the calibration capture zone is closely adjacent to the sample capture zone, so that the dynamics of the capillary action of the components of the assay are similar (e.g., essentially the same) at both the calibration capture zone and the sample capture zone. For example, the two capture zones are sufficiently close together such that the speed of the liquid flow is similar over both zones. Although they are closely adjacent, the calibration capture zone and the sample capture zone are also sufficiently spaced such that the particles arrested in each zone can be quantitated individually (e.g., without crosstalk). Furthermore, in a preferred embodiment, the sample capture zone is separated from the application point by a space that is a large distance, relative to the small distance between the sample capture zone and the calibration capture zone. Because particle capture is a rate limiting step in the assay, the distance between the application point and the capture zones (where particles are captured) must be sufficient to retard the speed of the liquid flow to a rate that is slow enough to allow capture of particles when the liquid flow moves over the sample capture zone. The optimal distances between the components on the membrane strip can be determined and adjusted using routine experimentation.

The quantitative assay additionally uses a sample collection apparatus. The sample collection apparatus is not in fluid contact with the solid phase apparatus "Not in fluid contact,"

as used herein, indicates that fluid will not flow passively from the sample collection apparatus onto/into application point; rather, a positive action is necessary to allow fluid flow. For example, physical separation (separate location) or separation by a physical component (e.g., a membrane, a hydrophobic region that would prevent liquid flow) can be used.

A "sample collection apparatus," as used herein, refers to an apparatus that can be used for collection of the fluid sample or into which a collected fluid sample can be deposited or stored. The sample collection apparatus can be any apparatus which can contain binding particles as described below (e.g., binding particles, analyte binding particles, calibration analyte binding particles), and which can be added a measured volume of fluid sample. Representative sample collection apparatus include a sample tube, a test tube, a vial, a pipette or pipette tip, a syringe. In a preferred embodiment, the sample collection apparatus is a pipette or pipette tip.

In one embodiment, the sample collection apparatus contains a population of "binding particles" which are coated with the analyte binding agent and with the calibration analyte binding agent. In another embodiment, the sample collection apparatus contains a population of "analyte binding particles," which are coated with the analyte binding agent, and a population of "calibration analyte binding particles," which are coated with the calibration analyte binding agent. In either embodiment, the population of particles varies, depending on the size and composition of the particles, the composition of the membrane of the solid phase apparatus, and the level of sensitivity of the assay. The population typically ranges approximately between $1\times10^3$ and $1\times10^9$, although fewer or more can be used if desired. In certain embodiments the amount of particles is determined as an amount of solids in the suspension used to apply the particles for storage within the sample collection apparatus, as described below. For example, when applying the particles in solution for freeze- or vacuum-drying in the sample collection apparatus, a suspension of approximately 0.05% to 0.228% solids (W/V) in 5 µl of suspension can be used. Alternatively, other amounts can be used, including, for example, from approximately 0.01% to 0.5% (W/V).

The binding particles are particles which can be coated with the analyte binding agent (the second member of the analyte binding pair) and/or with the calibration analyte binding agent (the second member of the calibration analyte binding pair). In a preferred embodiment, the analyte binding particles are liposomes, colloidal gold, organic polymer latex particles, inorganic fluorescent particles or phosphorescent particles. In a particularly preferred embodiment, the particles are polystyrene latex beads, and most particularly, polystyrene latex beads that have been prepared in the absence of surfactant, such as surfactant-free Superactive Uniform Aldehyde/Sulfate Latexes (Interfacial Dynamics Corp., Portland, Oreg.).

The size of the particles is related to porosity of the membrane (for analytes in fluid samples) and also to the size of the analyte of interest (e.g., for particulate analytes): the particles must be sufficiently small to be transported along the membrane by capillary action of fluid, and also (for solid, e.g., particulate analytes, sufficiently small for the complex of contacted binding particles, as described below, to be transported along the membrane by capillary action). The particles can be labeled to facilitate detection. The particles are labeled by a means which does not significantly affect the physical properties of the particles; for example, the particles are labeled internally (that is, the label is included within the particle, such as within the liposome or inside the polystyrene latex bead). Representative labels include luminescent labels; chemiluminescent labels; phosphorescent labels; fluorescent labels; phosphorescent labels; enzyme-linked labels; chemical labels, such as electroactive agents (e.g., ferrocyanide); and colorimetric labels, such as dyes. In one embodiment, a fluorescent label is used. In another embodiment, phosphorescent particles are used, particularly "up-converting" phosphorescent particles, such as those described in U.S. Pat. No. 5,043,265.

In a first embodiment, the collection apparatus contains particles that are coated with an analyte binding agent that is a second member of the analyte binding pair. As described above, the analyte binding agent (second member of the analyte binding pair) specifically and preferentially binds to the analyte of interest (first member of the analyte binding pair). Representative analyte binding agents include antibodies (or fragments thereof); haptens; drug conjugates; receptors; or other binding partners. In one preferred embodiment, the analyte binding agent is an antibody to the analyte of interest. Antibodies can be monoclonal antibodies or polyclonal antibodies. The term "antibody", as used herein, also refers to antibody fragments which are sufficient to bind to the analyte of interest. Alternatively, in another embodiment, molecules which specifically bind to the analyte of interest, such as engineered proteins having analyte binding sites, can also be used (Holliger, P. and H. R. Hoogenbloom, *Trends in Biotechnology* 13:7-9 (1995); Chamow, S. M. and A. Ashkenazi, *Trends in Biotechnology* 14:52-60:1996)). In still another embodiment, if the analyte of interest is a drug, a hapten or other drug conjugate can be used as the analyte binding agent. Alternatively, in a further embodiment, a receptor which binds to the analyte can be used (e.g., if the analyte of interest is a ligand). If the analyte is an antibody of known specificity, the particles can be coated with the antigen against which the analyte-antibody is directed, or can be coated with antibody to the analyte-antibody. Furthermore, because the analyte and the analyte binding agent form a binding pair, compounds or molecules described as representative analytes can also serve as analyte binding agents, and those described as representative analyte binding agents can similarly serve as analytes, as described herein.

In one embodiment, the particles are also coated with a calibration analyte binding agent that is a second member of the calibration analyte binding pair. As described above, the calibration analyte binding agent (second member of the calibration analyte binding pair) specifically and preferentially binds to the calibration analyte (first member of the calibration analyte binding pair). Representative calibration analyte binding agents include those types of binding agents described above with regard to analyte binding agents, including antibodies (or fragments thereof); haptens; drug conjugates; receptors; or other binding partners. In one preferred embodiment, the calibration analyte binding agent is an antibody to the calibration analyte. Antibodies can be monoclonal antibodies or polyclonal antibodies, as described above. In still another embodiment, if the calibration analyte is a drug, a hapten or other drug conjugate can be used as the calibration analyte binding agent. Alternatively, in a further embodiment, a receptor which binds to the calibration analyte can be used (e.g., if the calibration analyte is a ligand). If the calibration analyte is an antibody of known specificity, the particles can be coated with the antigen against which the analyte-antibody is directed, or can be coated with antibody to the analyte-antibody. Furthermore, because the calibration analyte and the calibration analyte binding agent form a binding pair, compounds or molecules described as representative calibration analytes can also serve as calibration analyte binding agents, and those described as representative calibration analyte binding agents can similarly serve as calibration analytes, as described herein.

If the particles are coated both with analyte binding agent and calibration analyte binding agent, they can be prepared by mixing the analyte binding agent and calibration analyte binding agent in a conjugation buffer, so that a homogeneous solution is made. A covalent coupling onto the particles is then performed, resulting in random binding of the binding agents onto the particle, in proportion to the amounts in solution.

In a second embodiment, the sample collection apparatus contains a population of analyte binding particles coated with an analyte binding agent, as described above, and also contains a population of calibration analyte binding particles that are coated with a calibration analyte binding agent that is a second member of the calibration analyte binding pair. As described above, the calibration analyte binding agent (second member of the calibration analyte binding pair) specifically and preferentially binds to the calibration analyte (first member of the calibration analyte binding pair). Representative calibration analyte binding agents include those types of binding agents described above with regard to analyte binding agents, including antibodies (or fragments thereof); haptens; drug conjugates; receptors; or other binding partners. In one preferred embodiment, the calibration analyte binding agent is an antibody to the calibration analyte. Antibodies can be monoclonal antibodies or polyclonal antibodies, as described above. In still another embodiment, if the calibration analyte is a drug, a hapten or other drug conjugate can be used as the calibration analyte binding agent. Alternatively, in a further embodiment, a receptor which binds to the calibration analyte can be used (e.g., if the calibration analyte is a ligand). If the calibration analyte is an antibody of known specificity, the particles can be coated with the antigen against which the analyte-antibody is directed, or can be coated with antibody to the analyte-antibody. Furthermore, because the calibration analyte and the calibration analyte binding agent form a binding pair, compounds or molecules described as representative calibration analytes can also serve as calibration analyte binding agents, and those described as representative calibration analyte binding agents can similarly serve as calibration analytes, as described herein.

The binding particles (coated with both analyte binding agent and calibration analyte binding agent), or the analyte binding particles and the calibration analyte binding particles, are stored within the sample collection apparatus in a stable form. A "stable form," as the term is used herein, indicates a form in which the particles do not significantly change in chemical makeup or physical state during storage. The stable form can be a liquid, gel, or solid form. In preferred embodiments, the particles are evaporatively dried; freeze-dried; and/or vacuum-dried. The analyte binding particles and the calibration analyte binding particles are stored at the same location within the sample collection apparatus (e.g., applied as a homogeneous mixture to the location).

In one further embodiment of the invention, calibration antigen (as described above) is also stored within the sample collection apparatus in a stable form. If the sample collection apparatus contains the calibration antigen, then the calibration antigen is stored at a separate location in the sample collection apparatus from the binding particles or from the calibration antigen binding particles. If the calibration antigen is not stored within the sample collection apparatus, then it is present in a buffer used in the methods of the invention, as described below.

In a particularly preferred embodiment, the sample collection apparatus is a pipette tip in which the particles (and the calibration antigen, if applicable) are vacuum-dried or lyophilized.

To perform the assays, a sample to be assessed for the presence of the analyte of interest, as described above, is used. In one embodiment, the sample is introduced into (drawn into, poured into, or otherwise placed into) the sample collection apparatus. For example, in one embodiment, a fluid sample is drawn up into a sample collection apparatus that comprises a pipette tip. In the embodiment in which binding particles (coated with analyte binding agent and calibration analyte binding agent) are present in the collection apparatus, introduction of a fluid sample into the sample collection apparatus results in mixing of the fluid sample with the binding particles. If calibration analyte is also present in the collection apparatus, introduction of a fluid sample into the sample collection apparatus similarly results in mixing of the fluid with the calibration analyte (in addition to the binding particles). The mixing results in the formation of a mixed fluid sample comprising calibration analyte. If the binding particles (and the calibration analyte, if present) are evaporatively-, freeze- or vacuum-dried, the introduction of the fluid sample into the sample collection apparatus can result in rehydration and suspension of the binding particles (and the calibration analyte, if present) in the fluid sample.

In the embodiment in which the sample collection apparatus contains both analyte binding particles and calibration analyte binding particles, introduction of a fluid sample into the sample collection apparatus results in mixing of the fluid sample with both types of binding particles. As before, if calibration analyte is also present in the collection apparatus, introduction of the fluid sample into the sample collection apparatus similarly results in mixing of the fluid with the calibration analyte (in addition to the binding particles) and formation of a mixed fluid sample. If the analyte binding particles and/or the calibration analyte binding particles are evaporatively-, freeze- or vacuum-dried, the introduction of the fluid sample into the sample collection apparatus can result in rehydration and suspension of the particles (and the calibration analyte, if present) in the fluid sample.

A buffer (e.g., for dilution) is also introduced, forming a "buffered, mixed fluid sample." The buffered, mixed fluid sample can be formed either by dispensing the mixed fluid sample into a "buffer container" (e.g., test tube) containing the buffer, or by introducing the buffer into the sample collection apparatus prior to introducing a fluid sample. Alternatively, if desired, the buffer can be first introduced into the sample collection apparatus, followed by introduction of a fluid sample into the sample collection apparatus.

If the analyte of interest is a solid (e.g., a powder, a particulate; spore; or other particle, as described above), a fluid sample as described above can be prepared by introducing the solid into the buffer container; in this embodiment, the buffered, mixed fluid sample is formed by introducing the fluid sample (comprising the buffer) into the sample collection apparatus. In another embodiment, the buffer is introduced into the sample collection apparatus, followed by introduction of the sample into the sample collection apparatus.

The buffer can be an aqueous fluid that supports a reaction between the analyte of interest and the analyte binding agent (e.g., does not interfere with antibody/antigen interaction); and that has a viscosity that is sufficiently low to allow movement of the fluid by capillary action. In one embodiment, the buffer contains one or more of the following components: a buffering agent (e.g., phosphate); a salt (e.g., NaCl); a protein stabilizer (e.g., BSA, casein, serum); and/or a detergent such as a nonionic detergent or a surfactant (e.g., one or more of the following agents commonly available in surfactant tool kits: NINATE 411, Zonyl FSN 100, Aerosol OT 100%, GEROPON T-77, BIO-TERGE AS-40, STANDAPOL ES-1, Tetronic 1307, Surfnyol 465, Surfynol 485, Surfynol 104PG-50, IGEPAL CA210, TRITON X-45, TRITON X-100, TRITON X305, SILWET L7600, RHODASURF ON-870, Cremophor EL, TWEEN 20, TWEEN 80, BRIJ 35, CHEMAL LA-9, Pluronic L64, SURFACTANT 10G, SPAN 60, CREL). Optionally, if desired, the buffer can contain a thickening agent. Such components for buffers are commercially available. Representative buffers include, for example, saline, or 50 mM Tris-HCl, pH 7.2. Alternatively, water can be used in lieu of a buffered solution; as used herein, the term "buffer" refers to either a buffered solution or to water. If calibration analyte was not present in the sample collection apparatus, then calibration analyte is present in the buffer in a known amount. In certain embodiments, the calibration analyte can be present in the buffer in an amount such as 10-100 ng/ml.

To disperse the binding particles or the analyte binding particles and calibration analyte binding particles further into the fluid sample, if desired, the sample collection apparatus into which the fluid sample and the buffer has been introduced, or the buffer container into which the mixed fluid sample has been introduced, can be agitated (e.g., vortexed, shaken, pipetted down and up, etc.).

In one preferred embodiment, the sample collection apparatus comprises a pipette tip having vacuum-dried binding particles within its tip; the fluid sample is drawn into the pipette, thereby rehydrating the dried binding particles and forming a mixed fluid sample. In a particularly preferred embodiment, the mixed fluid sample is introduced into a buffer container, resulting in a buffered mixed fluid sample; the buffered mixed fluid sample in the buffer container is pipetted up and down using the sample collection apparatus, thereby further dispersing the analyte binding particles. In another preferred embodiment, the sample collection apparatus comprises a pipette tip having vacuum-dried analyte binding particles and vacuum-dried calibration analyte binding particles within its tip; the fluid sample is drawn into the pipette, thereby rehydrating both types of dried particles and forming a mixed fluid sample. In a particularly preferred embodiment, the mixed fluid sample is introduced into a buffer container, resulting in a buffered mixed fluid sample; the buffered mixed fluid sample in the buffer container is pipetted up and down using the sample collection apparatus, thereby further dispersing the analyte binding particles and calibration analyte binding particles.

The buffered, mixed fluid sample contains "contacted binding particles." The particles (either binding particles, or analyte binding particles and calibration analyte binding particles) are "contacted" in that they have been exposed to the analyte of interest (if it is present in the sample) and the calibration analyte. Contact allows binding to occur between the analyte of interest and the analyte binding agent (either on the binding particles or on the analyte binding particles), and also allows binding to occur between the calibration analyte and the calibration analyte binding agent (either on the binding particles or on the calibration analyte binding particles). "Binding" of analyte or of calibration analyte indicates that the analyte or calibration analyte interacts with (binds to) the analyte binding agent or to the calibration analyte binding agent, respectively. Contacted binding particles may or may not have analyte of interest bound to the analyte binding agent; similarly, contacted binding particles may or may not have calibration analyte bound to the calibration analyte binding agent.

Because there are multiple binding sites for calibration analyte on the binding particles or on the calibration analyte binding particles, the presence and the concentration of calibration analyte bound to each particle can vary; the concentration of calibration analyte bound to the particles increases proportionally with the amount of calibration analyte present in the fluid sample, and the probability of a particle being arrested in the calibration capture zone (as described below) similarly increases with increasing amount of calibration analyte bound to the calibration analyte binding agent on the particles. Thus, the population of contacted calibration analyte binding particles may comprise particles having various amount of calibration analyte bound to the calibration analyte binding agent, as well as particles having no calibration analyte bound to the calibration analyte binding agent (just as the particles initially have no calibration analyte bound to the calibration analyte binding agent). Furthermore, the degree of binding increases as the time factor of the conditions increases: while the majority of binding occurs within one minute (e.g., 60 seconds, preferably less than 60 seconds (e.g., 45 seconds, 30 seconds, or less), additional incubation (e.g., more than one minute (2 minutes, 5 minutes, 10 minutes, 15 minutes) results in additional binding. In preferred embodiments, the solution is mixed thoroughly to allow resuspension of particles and homogenization of the sample (e.g., in approximately 1-2 minutes). It is noted that the time kinetics are similar for the antigen binding agent and for the calibration analyte binding agent, so although binding will increase over time, the ratio (as discussed below) will remain the same.

If analyte of interest is present in the buffered, mixed fluid sample, binding occurs between the analyte and the analyte binding agent (either on the binding particles or on the analyte binding particles). Contacted binding particles (or contacted analyte binding particles) may or may not have analyte bound to the analyte binding agent, depending on whether or not analyte is present in the fluid sample and whether analyte has bound to the analyte binding agent on the binding particles or analyte binding particles. Because there are multiple binding sites for analyte on the binding particles or on the analyte binding particles, the presence and the concentration of analyte bound to particles varies; the concentration of analyte bound to the particles increases proportionally with the amount of analyte present in the fluid sample, and the probability of a particle being arrested in the sample capture zone (as described below) similarly increases with increasing amount of analyte bound to the analyte binding agent on the particles. Thus, the population of contacted binding particles may comprise particles having various amount of analyte bound to the analyte binding agent, as well as particles having no analyte bound to the analyte binding agent (just as the particles initially have no analyte bound to the analyte binding agent). Furthermore, the degree of binding increases as the time factor of the conditions increases: while the majority of binding occurs within one minute (e.g., 60 seconds, preferably less than 60 seconds (e.g., 45 seconds, 30 seconds, or less), additional incubation (e.g., more than one minute (2 minutes, 5 minutes, 10 minutes, 15 minutes) results in additional binding.

The buffered, mixed fluid sample is applied to the application point of the membrane strip of the solid phase apparatus, or to the application pad, if present. After the membrane strip is contacted with the buffered, mixed fluid sample, the membrane strip is maintained under conditions which allow fluid to move by capillary action to and through the membrane. The particles (and analyte, if present in the sample) move through the membrane as a result of capillary action of the fluid from the buffered, mixed fluid sample, to and through the "sample capture zone" on the membrane and subsequently to and through the "calibration capture zone." The membrane strip is maintained under conditions (e.g., sufficient time and fluid volume) which allow the particles to move by capillary action along the membrane to and through the sample capture zone and subsequently to the calibration capture zone, and subsequently beyond the capture zones (e.g., into a wicking pad), thereby removing any non-bound particles from the capture zones.

The movement of some of the binding particles (or analyte binding particles) is arrested by interaction of the sample capture reagent in the sample capture zone, with analyte of interest that is bound to the particles, resulting in immobilization of particles in the sample capture zone; the movement of some of the binding particles or calibration analyte binding particles is arrested by interaction of the calibration capture reagent in the calibration capture zone, with calibration analyte that is bound to the particles, resulting in immobilization of particles in the calibration capture zone. Capillary action subsequently moves any particles that have not been arrested in either the sample capture zone or the calibration capture zone, onwards beyond the calibration capture zone. In a preferred embodiment, the fluid moves any particles that have not been arrested in either capture zone into a wicking pad which follows the calibration capture zone.

If desired, a secondary wash step can be used. A buffer (e.g., the buffer described above) can be applied at the application point after the buffered, mixed fluid sample has soaked in to the membrane or into the application pad, if present. The secondary wash step can be used at any time thereafter, provided that it does not dilute the buffered, mixed fluid sample. A secondary wash step can contribute to reduction of background signal when the binding particles are detected, as described below.

The amount of particles arrested in the sample capture and the calibration capture zone are then detected. The particles are detected using an appropriate means for the type of label used on the particles. In a preferred embodiment, the amount of particles is detected by an optical method, such as by measuring the amount of fluorescence of the label of the particles. The amount of particles arrested in the calibration capture zone is detected in the same manner as the amount of particles in the sample capture zone. In a preferred embodiment, the amount is detected by an optical method, such as by measuring the amount of fluorescence of the label of the particles. Alternatively, the amount of particles can be detected using electrical conductivity or dielectric (capacitance). Alternatively, electrochemical detection of released electroactive agents, such as indium, bismuth, gallium or tellurium ions, as described by Hayes et al. (*Analytical Chem.* 66:1860-1865 (1994)) or ferrocyanide as suggested by Roberts and Durst (*Analytical Chem.* 67:482-491 (1995)) can be used. For example, if liposomes are used, ferrocyanide encapsulated within the liposome can be released by addition of a drop of detergent at the capture zone, and the released ferrocyanide detected electrochemically (Roberts and Durst, id.). If chelating agent-protein conjugates are used to chelate metal ions, addition of a drop of acid at the capture zone will release the ions and allow quantitation by anodic stripping voltametry (Hayes et al., id.).

In one embodiment, as described above, the amount of particles is represented by a curve that is directly related to the amount of label present at positions along the solid phase (e.g., the membrane strip). For example, the amount of particles at each position on the membrane strip (e.g., at the sample capture zone and the calibration capture zone, and/or areas in between or adjacent to the sample capture zone and the calibration capture zone, and/or other areas of the membrane strip) can be determined and plotted as a function of the distance of the position along the membrane strip. The amount of particles can then be calculated as a function of the area under the curve, which is related to the amount of label present.

A corrected particle amount is determined, and the amount of analyte can then be determined from the corrected particle amount using appropriate calculation. The corrected particle amount is based on the amount of particles arrested in the sample capture zone and in the calibration capture zone. For example, in one embodiment, the corrected particle amount is inversely proportional to a ratio (R) of the particle amount present in the sample capture zone to the particle amount present in the calibration capture zone. The amount of analyte present can be then determined from the corrected particle amount (the ratio), utilizing a standard curve. The standard curve is generated by preparing a series of calibration samples, containing known concentrations of the analyte of interest in the fluid in which the analyte is to be detected (such as serum depleted of the analyte). The assay can then performed on the series of calibration samples; the value of R is measured for each calibration sample; and the R values are plotted as a function of the concentration of analyte included in the calibration sample. Samples containing an unknown amount of analyte (the "test samples") are assayed by measuring the value of R for the test sample, and the concentration of analyte in the test sample is determined by referring to the standard curve. As above, one standard curve can be generated and used for all test samples in a lot (e.g., for all test samples using a specified preparation of test reagents); it is not necessary that the standard curve be re-generated for each test sample. In another embodiment, the corrected particle amount is inversely proportional to a ratio (R) of the amount of the particle amount present in the sample capture zone, to the sum of the particle amount present in the calibration capture zone and the particle amount present in the sample capture zone. The amount of analyte present can be then determined from corrected particle amount (the ratio), utilizing a standard curve. Alternatively, other ratios and/or standard curves can also be used to determine the amount of analyte in the sample. In addition, if desired, the amount of label that is present in the background can be subtracted from the analyte coated particle amount present in the sample capture zone and the analyte coated particle amount present in the calibration capture zone prior to calculation of the ratio (R).

Benefits of the Invention

The methods of the invention provide assays with enhanced sensitivity, when compared with assays in which the particles and the calibration agents are imbedded within the membrane of the solid phase apparatus. For the assays, because the fluid sample to be assayed for the analyte of interest is mixed with the binding particles or analyte binding particles prior to application to the membrane, there is a longer time for the analyte of interest to bind to the binding particles or to the analyte binding particles prior to the capture reaction which occurs in the membrane. Furthermore, because the interaction between the analyte of interest and the binding particles or analyte binding particles occurs in the fluid phase, it allows more efficient binding because of greater mobility of the particles, than the same interaction between analyte of interest and binding particles or analyte binding particles would be in the matrix of the membrane of the solid phase apparatus. In addition, the methods correct for effects of various environmental conditions, including temperature effects, humidity effects, and other conditions.

Also, a greater number of particles can be included in a fluid collection apparatus than would be possible to embed in a solid phase apparatus; the greater number further enhances the sensitivity of the reaction. In addition, because the analyte binding particles (or binding particles) are dispersed in the buffered, mixed fluid sample prior to application of the buffered, mixed fluid sample to the solid phase membrane, the particles pass over the capture zone(s) in a continuous manner through the capillary action of the fluid, rather than in a quick wave on the crest of a fluid front. As a result, a lower concentration of particles flows through the capture zone(s) for a longer time: thus the time during which particles can be "captured" is effectively increased, while the amount of particles that pass through the capture zone(s) is effectively lowered, thereby avoiding the blocking of capture of some particles by others which occurs when the particles pass on the crest of a fluid front.

In addition, the calibration reaction closely mimics the analyte of interest reaction, in that both reactions require two separate binding events: binding of analyte to analyte binding agent; and subsequent binding of analyte to capture reagent. The kinetics of the two binding events are extremely similar, and allow more accurate correction of binding particle amounts than would occur with a one-step calibration reaction.

Although the assays of the invention have been described particularly in relation to immunoassays, the assays can similarly be used with other binding pairs as described above (e.g., nucleic acids, receptor-ligands, lectin-sugars), using the same methods as described above with the desired components as the analyte and the analyte binding agent.

Kits of the Invention

The invention also includes kits for use in the methods described herein. Kit components can include: first and/or second members of a specific binding pair, buffers and/or buffer containers, fluid collection means, one or more solid phase apparatus (optionally comprising an application pad and/or wicking pad), at least one sample collection apparatus, one or more buffer containers, calibration samples for generation of a standard curve and/or other standard curve information, binding particles, analyte binding particles, calibration analyte binding particles, capture reagents, antibodies, tools to assist in collecting of samples to be assessed for analyte of interest (e.g., swabs), disposal apparatus (e.g., biohazard waste bags), and/or other information or instructions regarding the sample collection apparatus (e.g., lot information, expiration date, etc.).

The invention is further illustrated by the following examples, which are not intended to be limiting in any way.

EXAMPLE 1

Assays were performed to assess a two-step internal calibration reaction which was designed to mimic the reaction of the analyte of interest within a single test strip. The immunoassays were based on RAMP™ assays (Response Biomedical). Immunoassay strips were prepared by striping antibodies specific for the target antigen (Goat anti-CP4 polyclonal antibody J7413 provided by Monsanto Company) at the sample capture zone at 1 mg/ml, 1 ul/cm; and antibodies specific for the calibration analyte (Rabbit anti-OA polyclonal antibody provided by UK-MOD) at the calibration binding zone at 1 mg/ml, 1 ul/cm on Millipore HF-75 nitrocellulose membrane. The membrane was blocked using 0.1% PVA 9000 in 10 mM PB, pH5.5. After drying, the strips were cut and assembled inside a cartridge and a sample pad and wicking pad was placed on opposite ends of the strip. The same antibodies, as above, for the target antigen and the calibrator were covalently conjugated to fluorescently tagged latex beads at a concentration of 0.5 mg of antibody per 4 ml of latex. The latex conjugates were vacuum dried into pipette tips. A sample was prepared consisting of both the antigen of interest and the calibration analyte at 10 ng/ml in buffer consisting of PBS, BSA, and Cremophol EL detergent. The latex conjugates were introduced into the sample by reconstituting the dried latex in the sample buffer and the sample was applied onto the sample pad of the cartridges containing the assay strips. The cartridges were scanned on a reader after 14 minutes. We tested the assay at room temperature and 37° C. to determine the ability of the modified system to correct for temperature effects.

Figures 4, 5, 6:
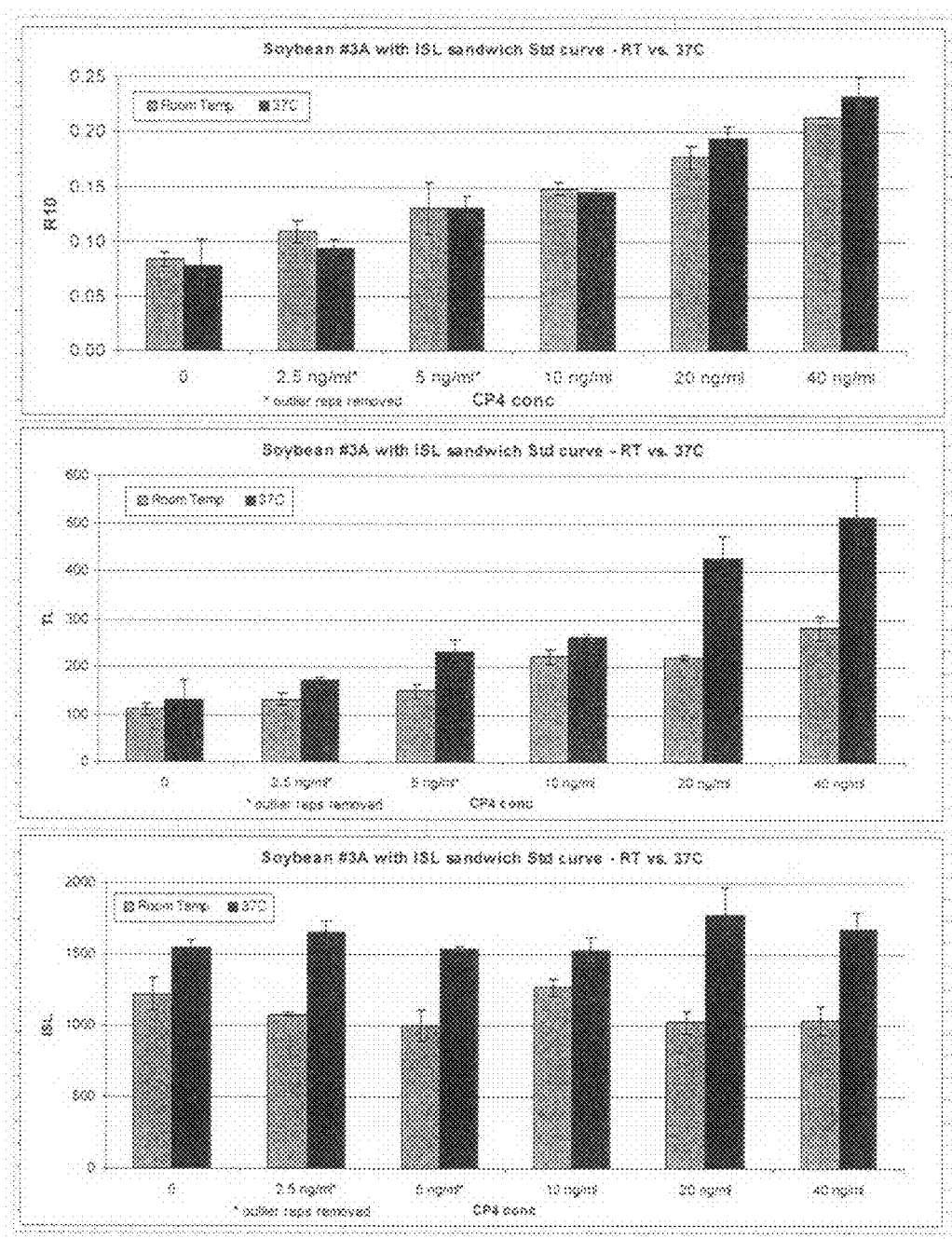
FIG. 4 is a graphic depiction of ratios of particles detected at the sample capture zone, to those detected at the calibration capture zone, indicating the presence of compensation for temperature effects. TL=Test Line (sample capture zone); ISL=Internal Standard Line (calibration capture zone); R10=Ratio (TL/TL+ISL).
FIG. 5 is a graphic depiction of the effect of temperature on capture of particles at the sample capture zone for a variety of concentrations of analyte.
FIG. 6 is a graphic depiction of the effect of temperature on capture of particles at the calibration capture zone for a variety of concentrations of analyte.

Results are shown in FIG. 1-6. TL=Test Line (sample capture zone); ISL=Internal Standard Line (calibration capture zone); R10=Ratio (TL/TL+ISL). FIG. 2 depicts the effect of temperature on capture of particles at the sample capture zone; FIG. 3 depicts the effect of temperature on capture of particles at the calibration capture zone. FIG. 1 depicts ratios that indicate the occurrence of compensation for temperature effects in the assays. FIG. 5 depicts the effect of temperature on capture of particles at the sample capture zone for a variety of concentrations of analyte; FIG. 6 depicts the effect of temperature on capture of particles at the calibration capture zone for a variety of concentrations of analyte; and FIG. 4 depicts ratios that indicate the occurrence of compensation for temperature effects in the assays.

EXAMPLE 2

In order to assess further the internal controls, a RAMP® BNP assay utilizing an anti-KLH calibration capture zone was assessed.

Overview of the RAMP® BNP Assay

The RAMP® BNP (B-type Natriuretic Protein) Assay is a quantitative immunochromatographic test for the determination of BNP levels in EDTA whole blood. Diluted EDTA whole blood was added to the sample well of a test cartridge which housed the immunochromatographic test strip (membrane strip). The red blood cells were retained in a sample pad, while the separated plasma migrated along the strip. Fluorescent-dyed latex particles coated with anti-BNP antibodies (binding particles) would bind to BNP, if present in the sample. As the sample migrated along the strip, BNP bound particles were immobilized at the sample capture zone, and additional particles were immobilized at the calibration capture zone. The RAMP Reader (Response Biomedical) then measured the amount of fluorescence emitted by the contacted binding particles bound at the sample capture zone and at the calibration capture zone. Using a ratio between the two fluorescence values, a quantitative reading was calculated and displayed by the reader.

The anti-KLH Calibration Capture Zone and the RAMP BNP Assay

Anti-human BNP monoclonal antibody obtained from Shionogi & Co., Ltd and KLH (Hemocyanin from Keyhole Limpets) obtained from Sigma-Aldrich Co. were covalently coupled to fluorescent-dyed latex particles at a ratio of 5 parts to 1 part. The resulting conjugate was diluted, then spotted and dried in assay specific reagent tips (RAMP BNP Assay Tip).

A second anti-human BNP monoclonal antibody obtained from Shionogi & Co., Ltd was striped onto mylar backed nitrocellulose membrane at the sample capture zone. Six mm above the sample capture zone, the same antibody amount of anti-KLH obtained from Sigma-Aldrich Co. was striped at the calibration capture zone. The nitrocellulose was then processed, cut and assembled into single-use, disposable plastic housings (RAMP BNP Test Cartridge) along with a sample pad at the distal end and an absorbent sink pad at the terminal end.

Using a supplied fixed volume pipette, the RAMP BNP Assay Tip was used to transfer an aliquot of the EDTA blood sample to a single-use Sample Buffer Vial. During a short mixing process, the assay specific reagents were released. Using the same pipette and tip, an aliquot of the prepared sample was introduced to the sample well of the RAMP BNP Test Cartridge.

Sample was metered onto the assay strip by a sample pad at the bottom of the sample well. As the sample was drawn by capillary action along the membrane, any target analyte (BNP) in the sample interacted and bound with the fluorescently dyed latex particles coated with analyte specific antibody and the KLH antigen (the binding particles), forming antibody/antigen complexes (e.g., one type of contacted binding particles). These labeled complexes were subsequently captured at the sample capture zone when BNP was present in the sample. Complexes not bound at the detection zone would continue to travel towards the terminal end of the assay strip where they would be captured by the anti-KLH calibration capture zone recognizing the KLH antigen also bound to the latex particles.

The absorbent pad at the terminal end of the assay strip soaked up excess sample. A section of the bottom of the Test Cartridge was open so that the test strip could be scanned by the fluorescence scanning Reader. After a fixed incubation period controlled by the Reader, the Reader scanned the test strip and measured fluorescence in the sample capture zone and the calibration capture zone. The absolute concentration of the BNP in the sample was determined by calculating a ratio between the two zones and referring it to a lot specific standard curve that resided in the Reader memory. The Reader integrated the area of fluorescence under each of the scan areas. The test result was then displayed on the RAMP Reader LCD.

RAMP BNP Assay with anti-KLH Calibration Capture Zone Example Data

Figure 7:
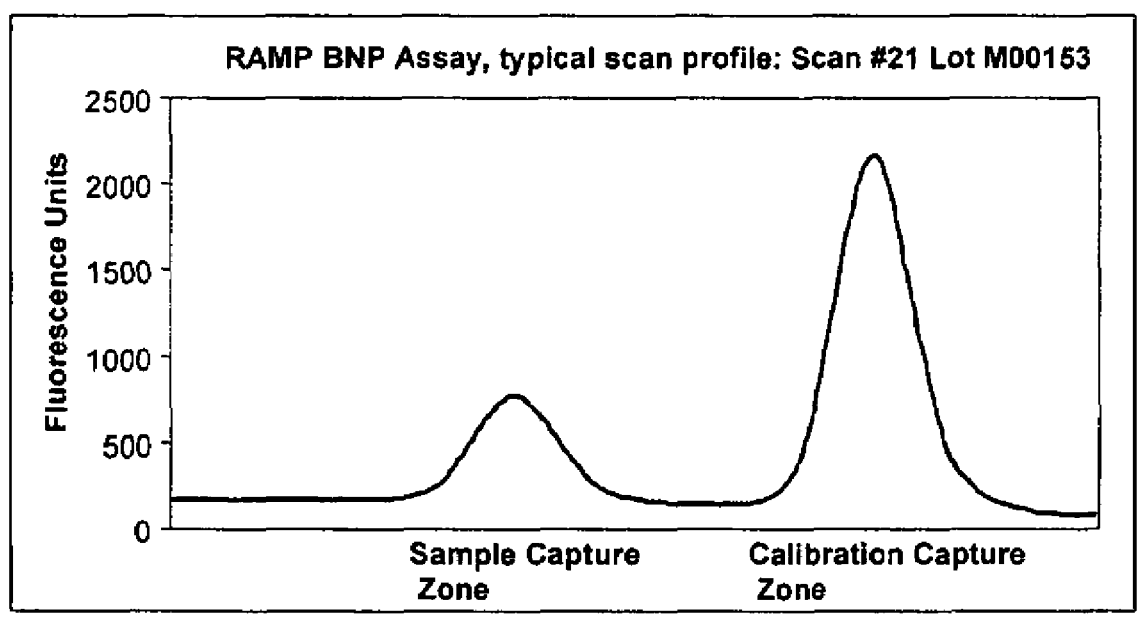
FIG. 7 is a graphic representation of fluorescence at the sample capture zone and the control capture zone for an assay detecting B-type Natriuretic protein (BNP).

FIG. 7 depicts a typical scan profile from the RAMP BNP Assay. After a fixed incubation period the Reader integrates the area of fluorescence under each of the scan areas.

Table 1 shows the integrated sample capture zone calibration capture zone values from which the RAMP Ratio was calculated for a typical RAMP BNP standard curve run at replicates of five at concentrations of 0, 4, 10, 40, 150, 600 and 2000 pg/mL BNP. A mathematical algorithm was then applied to the Ratio data to solve for BNP predicted values in units of pg/mL. It can be noted that as the concentration of BNP in the sample increased, so did the amount of binding at the sample capture zone, while the amount of binding at the calibration capture zone decreased. The calculated Ratio also increased.

TABLE 1

RAMP BNP Assay, Standard Curve Data

| Scan # | Sample (BNP pg/mL) | Sample Capture Zone | Calibration Capture Zone | Ratio | Prediction (BNP pg/mL) |
|---|---|---|---|---|---|
| 1 | 0 | 23 | 2778 | 492 | 0.0 |
| 2 | 0 | 23 | 3314 | 413 | 0.0 |
| 3 | 0 | 19 | 2737 | 413 | 0.0 |
| 4 | 0 | 9 | 2853 | 188 | 0.0 |
| 5 | 0 | 22 | 2905 | 450 | 0.0 |
| 6 | 4 | 39 | 2635 | 875 | 3.7 |
| 7 | 4 | 40 | 2978 | 795 | 3.0 |
| 8 | 4 | 29 | 2277 | 754 | 2.7 |
| 9 | 4 | 37 | 2596 | 843 | 3.5 |
| 10 | 4 | 35 | 2852 | 727 | 2.4 |
| 11 | 10 | 52 | 2638 | 1159 | 6.2 |
| 12 | 10 | 58 | 2692 | 1265 | 7.1 |
| 13 | 10 | 63 | 2776 | 1331 | 7.7 |
| 14 | 10 | 61 | 2929 | 1224 | 6.8 |
| 15 | 10 | 59 | 2698 | 1284 | 7.3 |
| 16 | 40 | 227 | 2783 | 4524 | 37.4 |
| 17 | 40 | 233 | 2840 | 4549 | 37.7 |
| 18 | 40 | 230 | 2799 | 4555 | 37.7 |
| 19 | 40 | 225 | 2749 | 4539 | 37.6 |
| 20 | 40 | 240 | 3179 | 4211 | 34.4 |
| 21 | 150 | 797 | 2508 | 14468 | 155.7 |
| 22 | 150 | 834 | 2942 | 13252 | 138.6 |
| 23 | 150 | 890 | 2880 | 14164 | 151.3 |
| 24 | 150 | 825 | 2782 | 13723 | 145.1 |
| 25 | 150 | 748 | 2511 | 13771 | 145.8 |
| 26 | 600 | 2177 | 1713 | 33578 | 618.2 |
| 27 | 600 | 2059 | 1732 | 32587 | 579.3 |
| 28 | 600 | 2351 | 1811 | 33892 | 631.1 |
| 29 | 600 | 2092 | 1751 | 32661 | 582.1 |
| 30 | 600 | 2007 | 1497 | 34366 | 651.2 |
| 31 | 2000 | 3619 | 823 | 48883 | 1988.0 |
| 32 | 2000 | 3713 | 846 | 48865 | 1984.5 |
| 33 | 2000 | 3498 | 729 | 49652 | >2000 |
| 34 | 2000 | 3799 | 908 | 48425 | 1901.0 |
| 35 | 2000 | 3673 | 826 | 48984 | >2000 |

The teachings of all patents, published applications and references cited herein are incorporated by reference in their entirety While this invention has been particularly shown and described with references to preferred embodiments thereof, it will be understood by those skilled in the art that various changes in form and details may be made therein without departing from the scope of the invention encompassed by the appended claims.

What is claimed is:

1. A method for quantitatively measuring the amount of an analyte of interest in a sample, comprising:
   a) providing a solid phase apparatus comprising a membrane strip comprising an application point, a sample capture zone and a calibration capture zone, wherein the sample capture zone is between the application point and the calibration capture zone;
   b) providing a sample collection apparatus that is not in fluid contact with the solid phase apparatus, the sample collection apparatus containing:
      i) a population of binding particles, wherein the binding particles are coated with both an analyte binding agent and a calibration analyte binding agent, and
      ii) a calibration analyte,
      wherein the population of binding particles is located at a different place in the sample collection apparatus from the calibration analyte;
   c) either i) introducing the sample into the sample collection apparatus, and subsequently introducing a buffer into the sample collection apparatus; or ii) introducing a buffer into the sample collection apparatus, and subsequently introducing the sample into the sample collection apparatus, thereby producing a buffered, mixed fluid sample containing contacted binding particles, the contacted binding particles comprising: binding particles having calibration analyte bound thereon and/or having analyte of interest bound thereon; and/or binding particles having neither calibration analyte nor analyte of interest bound thereon;

d) applying the buffered, mixed fluid sample to the application point of the membrane strip;

e) maintaining the membrane strip under conditions which allow fluid to transport contacted binding particles by capillary action through the strip to and through the sample capture zone, the sample capture zone having a sample capture reagent immobilized thereon, wherein the sample capture reagent can bind to analyte of interest; and allow binding of the sample capture reagent to analyte bound on the binding particles, thereby resulting in immobilization of binding particles in the sample capture zone;

f) further maintaining the membrane strip under conditions which allow fluid to transport contacted binding particles by capillary action through the strip to and through the calibration capture zone, the calibration capture zone having a calibration capture reagent immobilized thereon, wherein the calibration capture reagent can bind to the calibration analyte; and allow binding of the calibration capture reagent to calibration analyte bound on the binding particles, thereby resulting in immobilization of binding particles in the calibration capture zone;

g) further maintaining the membrane strip under conditions which allow the fluid in the sample to transport contacted binding particles not immobilized in the sample capture zone or in the calibration zone, by capillary action beyond the calibration capture zone;

h) determining the amount of binding particles in the sample capture zone and the amount of binding particles in the calibration capture zone;

i) determining a corrected binding particle amount from the amount of binding particles in the sample capture zone and the amount of binding particles in the calibration capture zone, wherein the amount of analyte of interest in the sample is directly related to the corrected binding particle amount.

2. The method of claim 1, wherein the corrected binding particle amount is determined as a ratio of the amount of binding particles in the sample capture zone, to the amount of binding particles in the calibration capture zone.

3. The method of claim 1, wherein the corrected binding particle amount is determined as a ratio of the amount of binding particles in the sample capture zone, to the sum of the amount of binding particles in the calibration capture zone and the amount of binding particles in the sample capture zone.

4. The method of claim 1, wherein the analyte binding agent is an antibody.

5. The method of claim 1, wherein the calibration analyte binding agent is an antibody.

6. A method for quantitatively measuring the amount of an analyte of interest in a sample, comprising:

a) providing a solid phase apparatus comprising a membrane strip comprising an application point, a sample capture zone and a calibration capture zone, wherein the sample capture zone is between the contact region and the calibration capture zone;

b) providing a sample collection apparatus that is not in fluid contact with the solid phase apparatus, the sample collection apparatus containing a population of binding particles, wherein the binding particles are coated with both an analyte binding agent and a calibration binding agent;

c) either i) introducing the sample into the sample collection apparatus, and subsequently introducing a buffer into the sample collection apparatus; or ii) introducing a buffer into the sample collection apparatus, and subsequently introducing the sample into the sample collection apparatus, wherein the buffer contains a calibration analyte, thereby producing a buffered, mixed fluid sample containing contacted binding particles, the contacted binding particles comprising: binding particles having calibration analyte bound thereon and/or having analyte of interest bound thereon; and/or binding particles having neither calibration analyte nor analyte of interest bound thereon;

d) applying the buffered, mixed fluid sample to the application point of the membrane strip;

e) maintaining the membrane strip under conditions which allow fluid to transport contacted binding particles by capillary action through the strip to and through the sample capture zone, the sample capture zone having a sample capture reagent immobilized thereon, wherein the sample capture reagent binds to analyte of interest; and allow binding of the sample capture reagent to analyte bound on the binding particles, thereby resulting in immobilization of binding particles in the sample capture zone;

f) further maintaining the membrane strip under conditions which allow the fluid in the sample to transport contacted binding particles by capillary action through the strip to and through the calibration capture zone, the calibration capture zone having a calibration capture reagent immobilized thereon, wherein the calibration capture reagent binds to the calibration analyte; and allow binding of the calibration capture reagent to calibration analyte bound on the binding particles, thereby resulting in immobilization of binding particles in the calibration capture zone;

g) further maintaining the membrane strip under conditions which allow the fluid in the sample to transport any contacted binding particles not immobilized in the sample capture zone or in the calibration zone by capillary action beyond the calibration capture zone;

h) determining the amount of binding particles in the sample capture zone and the amount of binding particles in the calibration capture zone;

i) determining a corrected binding particle amount from the amount of binding particles in the sample capture zone and the amount of binding particles in the calibration capture zone, wherein the amount of analyte of interest in the sample is directly related to the corrected binding particle amount.

7. The method of claim 6, wherein the corrected binding particle amount is determined as a ratio of the amount of binding particles in the sample capture zone, to the amount of binding particles in the calibration capture zone.

8. The method of claim 6, wherein the corrected binding particle amount is determined as a ratio of the amount of binding particles in the sample capture zone, to the sum of the amount of binding particles in the calibration capture zone and the amount of binding particles in the sample capture zone.

9. The method of claim 6, wherein the analyte binding agent is an antibody.

10. The method of claim 6, wherein the calibration analyte binding agent is an antibody.

11. The method of claim 1, wherein determining a corrected binding particle amount from the amount of binding particles in the sample capture zone and the amount of binding particles in the calibration capture zone includes subtracting an amount of background label from the amount of binding particles in the sample capture zone and from the amount of binding particles in the calibration capture zone.

12. The method of claim 6, wherein determining a corrected binding particle amount from the amount of binding particles in the sample capture zone and the amount of binding particles in the calibration capture zone includes subtracting an amount of background label from the amount of binding particles in the sample capture zone and from the amount of binding particles in the calibration capture zone.

\* \* \* \* \*